United States Patent [19]

Gordon

[11] Patent Number: 4,735,934

[45] Date of Patent: Apr. 5, 1988

[54] METHOD OF THERAPEUTICALLY TREATING A WARM BLOODED ANIMAL AFFLICTED WITH AN AUTOIMMUNE DISEASE

[75] Inventor: Paul Gordon, Chicago, Ill.

[73] Assignee: Greenwich Pharmaceuticals Incorporated, Greenwich, Conn.

[21] Appl. No.: 923,205

[22] Filed: Oct. 27, 1986

Related U.S. Application Data

[60] Division of Ser. No. 473,264, Mar. 14, 1983, which is a continuation of Ser. No. 234,505, Feb. 17, 1981, abandoned, which is a continuation of Ser. No. 122,742, Feb. 19, 1980, abandoned, which is a continuation of Ser. No. 845,788, Oct. 26, 1977, abandoned.

[51] Int. Cl.$^4$ .............................................. A61K 31/70
[52] U.S. Cl. .................................... 514/25; 514/825; 514/861
[58] Field of Search ......................... 514/25, 825, 861

[56] References Cited

U.S. PATENT DOCUMENTS 4,251,520 2/1981 Bruzzese et al. ...................... 536/4

Primary Examiner—Ronald W. Griffin
Attorney, Agent, or Firm—Finnegan, Henderson, Farabow, Garrett & Dunner

[57] ABSTRACT

The invention provides a method of therapeutically treating a warm blooded animal afflicted with an autoimmune disease such as rheumatoid arthritis. In one variant, this is accomplished by administering an ethereally monosubstituted monosaccharide having the general formula $M_1$—O—Y, and/or an ethereal monosubstitution of monosaccharide derivatives having the general formula $M_2$—O—Y, and/or pharmaceutically acceptable organic acid and inorganic acid salts thereof as defined hereinafter. In a preferred variant, a synergistic mixture is used containing one or more of the foregoing compounds as a first ingredient and an additional compatible substance as a second ingredient which is effective to therapeutically treat autoimmune diseases in warm blooded animals. The invention further provides a novel synergistic composition for therapeutically treating warm blooded animals afflicted with an autoimmune disease which consists essentially of the aforementioned first and second ingredients.

19 Claims, No Drawings

METHOD OF THERAPEUTICALLY TREATING A WARM BLOODED ANIMAL AFFLICTED WITH AN AUTOIMMUNE DISEASE

This is a divisional of U.S. application Ser. No. 473,264 filed Mar. 14, 1983, which is a continuation of U.S. application Ser. No. 234,505, filed Feb. 17, 1981, now abandoned, which is a continuation of U.S. application Ser. No. 122,742, filed Feb. 19, 1980, now abandoned, which was a continuation of U.S. application Ser. No. 845,788, filed Oct. 26, 1977, now abandoned.

THE BACKGROUND OF THE INVENTION

1. The Field of the Invention

The present invention is concerned with a method of therapeutically treating warm blooded animals afflicted with an autoimmune disease. In another variant, the invention further relates to a synergistic composition for therapeutically treating warm blooded animals afflicted with an autoimmune disease.

2. The Prior Art

Warm blooded animals in general, and especially man and lower mammals, often contract autoimmune-type diseases which are well known and recognized by the medical profession. The autoimmune diseases appear to involve a malfunctioning of the natural immune system wherein the afflicted animal develops immunity to its own cells or tissues, such as the synovial membrane of the joints in rheumatoid arthritis. While the present invention is not limited to the therapeutic treatment thereof, some specific examples of autoimmune diseases include rheumatoid arthritis, rheumatic fever, eczema and lupus erythematosis.

A wide variety of therapeutic treatments have been proposed heretofore for use in treating the aforementioned autoimmune diseases. Examples of some of the more common prior art drugs include (1) aspirin and other related pharmaceutically acceptable lower carboxylic acid salicylates wherein the carboxylic acid contains 1–8 and preferably 2–4 carbon atoms, for the treatment of rheumatoid arthritis and rheumatic fever, (2) phenylbutazone and indomethacin as a treatment for rheumatoid arthritis (c) adrenocorticosteroids for the treatment of rheumatoid arthritis, rheumatic fever and lupus erythematosis, and (4) levamisole for the treatment of rheumatoid arthritis, eczema, and lupus erythematosis. However, these prior art medications have not been entirely satisfactory or generally effective heretofore. As a result, a substantial percentage of the population continues to be afflicted with an autoimmune disease such as rheumatoid arthritis.

In the view of the foregoing, it is apparent that the prior art has long sought an entirely satisfactory method and composition for therapeutically treating autoimmune diseases in warm blooded animals. However, in spite of the long standing and great need therefor, such a method and composition were not available prior to the present invention.

THE SUMMARY OF THE INVENTION INCLUDING CERTAIN OBJECTS THEREOF

In accordance with one variant of the invention, autoimmune diseases in warm blooded animals are therapeutically treated by administering a therapeutically effective amount of an ethereally monosubstituted monosaccharide having the general formula $M_1$—O—Y, and/or an ethereal monosubstitution of monosaccharide derivatives having the general formula $M_2$—O—Y, and/or a pharmaceutically acceptable organic acid or inorganic acid salt thereof. In practicing another variant of the invention, a synergistic composition containing one or more of the foregoing compounds as a first ingredient and a second therapeutically active ingredient for treating autoimmune diseases is administered to the warm blooded animals. Novel synergistic compositions containing the aforementioned first and second ingredients are also provided for use in practicing the latter method of the invention. The aforementioned methods and synergistic compositions are very effective in overcoming the longstanding problems and deficiencies of the prior art discussed above.

It is an object of the present invention to provide a novel method of therapeutically treating a warm blooded animal afflicted with an autoimmune disease.

It is a further object to provide a novel method of therapeutically treating autoimmune diseases in warm blooded animals by administering a synergistic combination of drugs.

It is still a further object to provide a synergistic composition containing two or more therapeutically active ingredients which is especially useful in practicing the method of the invention.

Still other objects and advantages of the invention will be apparent to those skilled in the art upon reference to the following detailed description and the specific examples.

THE DETAILED DESCRIPTION OF THE INVENTION INCLUDING PRESENTLY PREFERRED VARIANTS THEREOF

In practicing the presently preferred variant of the method of the invention, warm blooded animals afflicted with an autoimmune disease are treated by administering a therapeutically effective amount of a substance which comprises at least one ethereally monosubstituted monosaccharide having the general formula $M_1$—O—Y, and/or at least one ethereal monosubstitution of monosaccharide derivatives having the general formula $M_2$—O—Y, and/or at least one pharmaceutically acceptable organic acid or inorganic acid salt of the foregoing compounds. In practicing another presently preferred variant of the method of the invention, autoimmune diseases in warm blooded animals are therapeutically treated by administering a synergistic composition containing one or more of the aforementioned compounds as a first ingredient, and as a second ingredient, an additional substance which is therapeutically effective to treat the autoimmune disease when administered alone to the warm blooded animal and which is therapeutically compatible with the first ingredient. In accordance with a further presently preferred variant of the invention, synergistic compositions containing the aforementioned first and second ingredients are provided which are especially useful in practicing the latter method of the invention.

In the foregoing general formulae, $M_1$ is the residue of a nonderivatized monosaccharide selected from the group consisting of pentoses, hexoses and heptoses, and $M_2$ is the residue of a monosaccharide selected from the group consisting of pentoses, hexoses and heptoses which has been derivatized with (a) one or more alcohols containing 1–18 carbon atoms and preferably 1–4 carbon atoms to produce an ether group at one or more available hydroxyl groups or residua, (b) one or more aldehydes containing 1–18 carbon atoms and preferably 1-4 carbon atoms to produce single or multiple acetal groups at one or more available hydroxyl groups or residua, (c) one or more ketones containing 1-18 carbon atoms and preferably 1-4 carbon atoms to produce single or multiple ketal groups at one or more available hydroxyl groups or residua, or (d) one or more organic acid residua containing 1-18 carbon atoms and preferably 1-4 carbon atoms to produce ester groups at one or more available hydroxyl groups or residua. The above alcohols, aldehydes, ketones and acids may be either open or closed chain compounds, saturated or unsaturated, and substituted or unsubstituted. In each instance, Y is selected from the group consisting of cyclic monovalent nitrogen-containing organic radicals and residua free of oxygen attached only to a ring carbon atom and derived from a substance other than a monosaccharide, and monovalent organic radicals and residua having the general formula

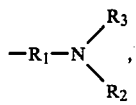

wherein $R_1$ is a divalent organic radical having a carbon chain length of about 1-7 carbon atoms and $R_2$ and $R_3$ are selected from the group consisting of —H, —OH, —SH, halogen and monovalent organic radicals and residua having a carbon chain length of about 1-7 carbon atoms. When $R_2$ or $R_3$ is halogen, the halogen may be F, Cl, Br, or I, of which Cl and Br is usually preferred. The organic radical $R_1$, and $R_2$ and $R_3$ when they are organic radicals, may be branched or unbranched carbon chains and may be saturated or unsaturated, and when saturated, the unbranched and/or branched carbon chains may contain one or more double or triple carbon-to-carbon bonds. The unbranched and/or branched carbon chains of $R_1$, $R_2$ and $R_3$ may be substituted or unsubstituted, and when substituted, one or more substituents may be present, such as —OH, —SH, halogen (F, Cl, Br and/or I), branched or unbranched and saturated or unsaturated hydrocarbon radicals containing 1-7 and preferably 1-3 carbon atoms, —$OR_4$ and/or —$SR_4$ radicals, wherein $R_4$ is a branched or unbranched and saturated or unsaturated hydrocarbon radical containing 1-7 and preferably 1-3 carbon atoms, carboxylic acid residua containing 1-7 and preferably 1-3 carbon atoms, and amino groups and aminohydrocarbon radicals containing 1-7 and preferably 1-3 carbon atoms. Preferably $R_1$ is a hydrocarbon radical having a carbon chain length of 1-3 or 1-4 carbon atoms and $R_2$ and $R_3$ are individually selected from the group consisting of hydrogen and/or hydrocarbon radicals having carbon chain lengths of 1-3 or 1-4 carbon atoms.

Examples of compounds from which cyclic organic radicals and residua are derived include (a) monovalent nitrogen containing saturated, unsaturated or aromatic carbocyclic compounds containing about 4-8 carbon atoms in the ring and preferably about 5-6 carbon atoms in the ring and at least one nitrogen atom attached thereto or to an organo substituent thereon, (b) heterocyclic organic compounds containing about 3-8 carbon atoms in the ring and at least one ring nitrogen atom and (c) derivatives of the foregoing compounds wherein at least one substituent is present, such as —OH, —SH, halogen (F, Cl, Br and/or I), branched or unbranched and saturated or unsaturated hydrocarbon radicals containing 1-7 and preferably 1-3 carbon atoms, —$OR_5$ and/or —$SR_5$ radicals wherein $R_5$ is a branched or unbranched and saturated or unsaturated hydrocarbon radical containing 1-7 and preferably 1-3 carbon atoms, carbocyclic acid residua containing 1-7 and preferably 1-3 carbon atoms, and amino groups and aminohydrocarbon radicals containing 1-7 and preferably 1-3 carbon atoms. The aforementioned cyclic organic radicals and residua should be free of oxygen attached only to a ring carbon atom and also should be derived from a substance other than a monosaccharide.

The nonderivatized monosaccharide residue $M_1$ may exist in an open chain or cyclic form illustrated by the following general formulae:

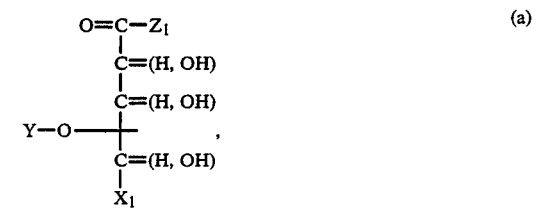

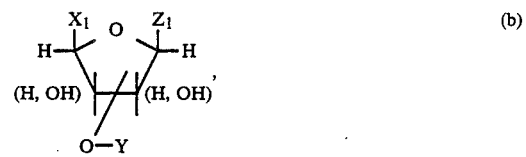

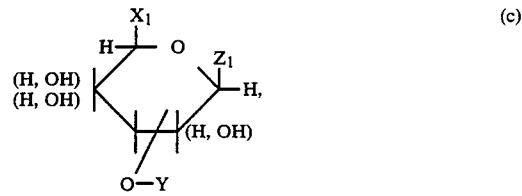

wherein $X_1$ and $Z_1$ are H, OH and/or hydroxyalkyl groups containing up to 3 carbon atoms, Y represents the same organic radicals and residua as aforementioned, and one of the OH groups, $X_1$ or $Z_1$ in each formula is replaced by —O—Y. The above general formulae (b) and (c) illustrate the pentacyclic and hexacyclic forms of the various isomers of the pentoses hexoses and heptoses, the relative spatial configuration of the —H, and —OH groups about the rings, and the monosubstitution thereof in accordance with one presently preferred variant of the invention. The hydroxyl group of the hemiacetal or hemiketal linkage may assume an $\alpha$ or a $\beta$ configuration and the compounds may be in the form of anomers or mixtures of anomers.

The derivatized monosaccharide residue $M_2$ may exist in an open chain or cyclic form illustrated by the following general formulae:

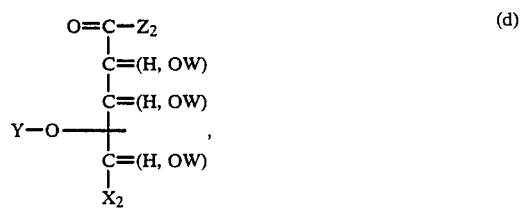

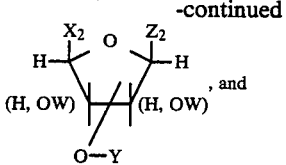
, and

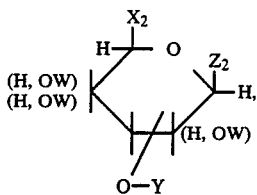

wherein $X_2$ and $Z_2$ are H, —OH, hydroxyalkyl, alkoxyl and/or alkoxyalkyl groups containing up to 3 carbon atoms, W is H, alkyl, alkenyl, cyclic alkane or cyclic aromatic groups containing 1–18 and preferably 1–6 carbon atoms or acyl groups containing 1–18 and preferably 1–4 carbon atoms, Y represents the same organic radicals and residua as aforementioned, and one of the OW groups $X_2$ or $Z_2$ in each formula is replaced by —O—Y. The above general formulae illustrate the various isomers of the pentoses, hexoses and heptoses, the relative spatial configuration of the —H and —OH groups about the ring and the derivatization thereof in accordance with one presently preferred variant of the invention. The hydroxyl or alkoxyl residue of the hemiacetal or hemiketal linkage may assume an α or a β configuration, and the derivatized monosaccharide may be in form of anomers or mixtures of anomers.

The configuration of the various isomers and derivatives of the pentoses, hexoses and heptoses are well known to those skilled in this art and numerous reference books are available on the subject, the teachings of which are incorporated herein by reference, for example *Textbook of Biochemistry*, 4th Edition. by West et al (1966) and *The Monosaccharides* by Stanek, Cerny, Kocourek and Pacak (1963). The prior art discloses, for example, a total of eight open chain isomers for the reducing hexoses, and an even larger number of open chain isomers for the reducing heptoses. Either the dextrorotatory or D-series or the levorotatory or L-series of the pentoses, hexoses and heptoses may be used in practicing the invention, but it is usually preferred to use the D-series. The hexoses often give the best results and especially D-talose, D-galactose, L-galactose, D-idose, D-gulose, D-mannose, D-glucose, L-glucose, D-altrose and D-allose. The aforementioned pentoses, hexoses and heptoses may be derivatized at one or more of the hydroxyl groups, and is then ethereally substituted at one remaining available reactive position or positions. The ethereal substitution of certain available reactive positions of specific monosaccharide derivatives results in more therapeutically active or less toxic compounds. For instance, substitution of the 1-O- and 3-O-positions of glucose and the 6-O-position of galactose results in especially valuable compounds. Additionally, the ethereal substitution of the 3-O-position of 1,2-O-isopropylidene-D-glucofuranose or 1,2:5,6-di-O-isopropylidene-D-glucofuranose and the 6-O-position of 1,2-O-isopropylidene-D-galactopyranose or 1,2:3,4-di-O-isopropylidene-D-galactopyranose results in especially valuable compounds.

The following substituents, i.e., Y in the aforementioned general formulae $M_1$—O—Y or $M_2$—O—Y, may be ethereally substituted on any of the available reactive positions of the various isomers of the pentoses, hexoses and heptoses of $M_1$ or $M_2$ to produce nontoxic compounds having exceptional activity for the purposes of the present invention:

-(n-propylamino),
-(N',N'-dimethylamino-n-propyl),
-(N',N'-dimethylaminoisopropyl),
-(N'-methylpiperidyl),
-(N',N'-dimethylaminoethyl),
-(N',N'-diethylaminoethyl),
-(2',N',N'-trimethylamino-n-propyl),
-dimethylamino,
-(N',N'-dimethylaminomethyl),
-(N',N'-dimethylaminopropyl),
-(N',N'-dimethylamino-iso-butyl),
-(N',N'-dimethylamino-n-butyl),
-(N',N'-dimethylamino-iso-pentyl),
-(N',N'-dimethylaminopentyl),
-(N'-methylamino-n-propyl),
-(N'-methyl-N'-ethylamino-n-propyl),
-(N',N'-diethylamino-n-propyl),
-(amino-iso-propyl),
-(N'-ethylamino-n-propyl),
-(N'-propylamino-n-propyl),
-(N',N'-iso-propylamino-n-propyl),
-(1',2'-ethylamino-n-propyl),
-(1'-n-propylpyrrolidyl),
-(1'-n-propylpiperidyl),
-piperidyl, and
-(N',N'-dimethylamino-sec-butyl).

Of the foregoing, -(N',N'-dimethylamino-n-propyl) is presently preferred as Y in the formulae $M_1$—Y—O and $M_2$—O—Y and especially when substituted in the 1-O- or 3-O- position of glucose or in the 6-O- position of galactose, or when substituted in the 3-O- position of 1,2-O-isopropylidene-D-glucofuranose or 1,2:5,6-di-O-isopropylidene-D-glucofuranose or the 6-O- position of 1,2-O-isopropylidene-D-galactopyranose or 1,2:3,4-di-O-isopropylidene-D-galactopyranose.

The following compounds of the general formula $M_1$—O—Y have been found to have exceptional activity for use in the present invention:

3-O-3'-(n-propylamino)-glucose,
3-O-3'-(N',N'-dimethylamino-n-propyl)-glucose,
3-O-4'-(N-methyl piperidyl)-glucose,
3-O-2'-(N',N'-dimethylaminoethyl)-glucose,
3-O-2'-(N',N'-diethylaminoethyl)-glucose,
3-O-3'-(2',N',N'-trimethylamino-n-propyl)-glucose,
α-N',N'-dimethylaminoisopropyl-glucoside,
6-O-3'-(N',N'-dimethylamino-n-propyl)-galactose,
3-O-2'-(N',N'-dimethylaminopropyl)-glucose,
6-O-2'-(N',N'-dimethylaminopropyl)-galactose, and
pharmaceutically acceptable organic acid and inorganic acid salts thereof. The D-series of these compounds are preferred. Species of the foregoing compounds which are presently preferred as follows:

3-O-3'-(N',N'-dimethylamino-n-propyl)-D-glucopyranose,
3-O-4'-(N-methyl piperidyl)-D-glucopyranose,
3-O-2'-(N',N'-dimethylaminoethyl)-D-glucopyranose,
3-O-3'-(2',N'N'-trimethylamino-n-propyl)-D-glucopyranose,
α-N',N'-dimethylaminoisopropyl-D-glucoside,
6-O-3'-(N',N'-dimethylamino-n-propyl)-D-galactopyranose,
3-O-2'-(N',N'-dimethylaminopropyl)-D-galactopyranose, 6-O-2'-(N',N'-dimethylaminopropyl)-D-galactopyranose, and
pharmaceutically acceptable organic acid and inorganic acid salts thereof.

Additional compounds of the general formula $M_1$—O—Y, wherein Y is

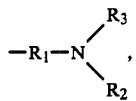

which may be used in practicing the invention are listed below:

| Monosaccharide Residue $M_1$ | Substituent (Y) | | |
|---|---|---|---|
| | $R_1$ | $R_2$ | $R_3$ |
| 3-O—D-glucofuranose | 3'-n-propyl | H | methyl |
| " | " | ethyl | " |
| " | " | H | ethyl |
| " | 2'-iso-propyl | methyl | methyl |
| " | 3'-1,2-propenyl | " | " |
| " | sec-butyl | " | " |
| " | 3'-butyl | " | " |
| " | 2'-ethyl | H | H |
| " | methyl | H | H |
| 6-O—D-galactopyranose | 3'-n-propyl | H | methyl |
| " | " | ethyl | " |
| " | " | H | ethyl |
| " | 3'-1,2-propenyl | methyl | methyl |
| " | 2'-iso-propyl | " | " |
| " | sec-butyl | " | " |
| " | 3'-butyl | " | " |
| " | 2'-ethyl | H | H |
| " | methyl | H | H |

Still other compounds of the general formula $M_1$—O—Y, wherein Y is cyclic monovalent nitrogen-containing organic radical or residue, which may be used in the method of the invention are as follows:

| Monosaccharide Residue $M_1$ | Substituent (Y) | |
|---|---|---|
| | Cyclic Radical | Substituent on the Cyclic Radical |
| 3-O—D-glucofuranose | 4'-piperidyl | H |
| " | 3'-piperidyl | methyl, H |
| " | 2'-piperidyl | methyl, H |
| " | 3'-pyrrolidyl | methyl, H |
| " | 2'-pyrrolidyl | methyl, H |
| 6-O—D-galactopyranose | 4'-piperidyl | H |
| " | 3'-piperidyl | methyl, H |
| " | 2'-piperidyl | methyl, H |
| " | 3'-pyrrolidyl | methyl, H |
| " | 2'-pyrrolidyl | methyl, H |

The following compounds of the general formula $M_2$—O—Y have exceptional wide spectrum activity and other valuable properties:
3-O-3'-(n-propylamino)-1,2-O-isopropylidene-D-glucofuranose,
3-O-3'-(N',N'-dimethylamino-n-propyl)-1,2-O-isopropylidene-D-glucofuranose,
3-O-4'-(N'-methylpiperidyl)-1,2-O-isopropylidene-D-glucofuranose,
3-O-2'-(N',N'-dimethylaminoethyl)-1,2-O-isopropylidene-D-glucofuranose,
3-O-2'-(N',N'-diethylaminoethyl)-1,2-O-isopropylidene-D-glucofuranose,
3-O-3'-(2',N',N'-trimethylamino-n-propyl)-1,2-O-isopropylidene-D-glucofuranose,
3-O-2'-(N',N'-dimethylaminopropyl)-1,2:5,6-di-O-isopropylidene-D-glucofuranose,
3-O-2'-(N',N'-dimethylaminopropyl)-1,2-O-isopropylidene-D-glucofuranose,
6-O-3'-(N',N'-dimethylamino-n-propyl)-1,2-O-isopropylidene-D-galactopyranose,
6-O-2'-(N',N'-dimethylaminopropyl)-1,2-O-isopropylidene-D-galactopyranose,
3-O-3'-(n-propylamino)-1,2:5,6-di-O-isopropylidene-D-glucofuranose,
3-O-3'-(N',N'-dimethylamino-n-propyl)-1,2:5,6-di-O-isopropylidene-D-glucofuranose,
3-O-4'-(N'-methylpiperidyl)-1,2:5,6-di-O-isopropylidene-D-glucofuranose,
3-O-2'-(N',N'-dimethylaminoethyl)-1,2:5,6-di-O-isopropylidene-D-glucofuranose,
3-O-2'-(N',N'-diethylaminoethyl)-1,2:5,6-di-O-isopropylidene-D-glucofuranose,
3-O-3'-(2',N',N'-trimethylamino-n-propyl)-1,2:5,6-di-O-isopropylidene-D-glucofuranose,
6-O-3'-(N',N'-dimethylamino-n-propyl)-1,2:3,4-di-O-isopropylidene-D-galactopyranose,
6-O-2'-(N',N'-dimethylaminopropyl)-1,2:3,4-di-O-isopropylidene-D-galactopyranose,
α-N',N'-dimethylamino-iso-propyl-2,3:5,6-di-O-isopropylidene-D-glucofuranoside, and organic and inorganic acid salts thereof.

Additional compounds of the general formula $M_2$—O—Y, wherein Y is

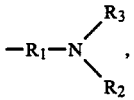

which may be used in the method of the invention are listed below:

| Monosaccharide Residue $M_1$ | Substituent (Y) | | |
|---|---|---|---|
| | $R_1$ | $R_2$ | $R_3$ |
| 3-O—1,2-O—isopropylidene-D-glucofuranose | 3'-n-propyl | H | methyl |
| 3-O—1,2-O—isopropylidene-D-glucofuranose | " | ethyl | " |
| 3-O—1,2-O—isopropylidene-D-glucofuranose | " | H | ethyl |
| 3-O—1,2-O—isopropylidene-D-glucofuranose | 2'-iso-propyl | methyl | methyl |
| 3-O—1,2-O—isopropylidene-D-glucofuranose | 3'-1,2-propenyl | " | " |
| 3-O—1,2-O—isopropylidene-D-glucofuranose | sec-butyl | " | " |
| 3-O—1,2-O—isopropylidene-D-glucofuranose | 3'-butyl | " | " |
| 3-O—1,2-O—isopropylidene-D-glucofuranose | 2'-ethyl | H | H |
| 3-O—1,2-O—isopropylidene-D-glucofuranose | methyl | H | H |
| 6-O—1,2-O—isopropylidene-D-galactopyranose | 3'-n-propyl | H | methyl |
| 6-O—1,2-O—isopropylidene-D-galactopyranose | " | ethyl | " |
| 6-O—1,2-O—isopropylidene-D-galactopyranose | " | H | ethyl |
| 6-O—1,2-O—isopropylidene-D-galactopyranose | 3'-1,2-propenyl | methyl | methyl |
| 6-O—1,2-O—isopropylidene-D-galactopyranose | 2'-iso-propyl | " | " |
| 6-O—1,2-O—isopropylidene-D-galactopyranose | sec-butyl | " | " |

-continued

| Monosaccharide Residue M₁ | Substitutent (Y) | | |
|---|---|---|---|
| | R₁ | R₂ | R₃ |
| 6-O—1,2-O—isopropylidene-D-galactopyranose | 3'-butyl | " | " |
| 6-O—1,2-O—isopropylidene-D-galactopyranose | 2'-ethyl | H | H |
| 6-O—1,2-O—isopropylidene-D-galactopyranose | methyl | H | H |
| 3-O—1,2:3,6-di-O—iso-propylidene-D-gluco furanose | 3'-n-propyl | H | methyl |
| 3-O—1,2:3,6-di-O—iso-propylidene-D-gluco furanose | " | ethyl | " |
| 3-O—1,2:3,6-di-O—iso-propylidene-D-gluco furanose | " | H | ethyl |
| 3-O—1,2:3,6-di-O—iso-propylidene-D-gluco furanose | 2'-iso-propyl | methyl | methyl |
| 3-O—1,2:3,6-di-O—iso-propylidene-D-gluco furanose | 3'-1,2-propenyl | " | " |
| 3-O—1,2:3,6-di-O—iso-propylidene-D-gluco furanose | sec-butyl | " | " |
| 3-O—1,2:3,6-di-O—iso-propylidene-D-gluco furanose | 3'-butyl | " | " |
| 3-O—1,2:3,6-di-O—iso-propylidene-D-gluco furanose | 2'-ethyl | H | H |
| 3-O—1,2:3,6-di-O—iso-propylidene-D-gluco furanose | methyl | H | H |
| 6-O—1,2:3,4-di-O—iso-propylidene-D-galactopyranose | 3'-n-propyl | H | methyl |
| 6-O—1,2:3,4-di-O—iso-propylidene-D-galactopyranose | " | ethyl | " |
| 6-O—1,2:3,4-di-O—iso-propylidene-D-galactopyranose | " | H | ethyl |
| 6-O—1,2:3,4-di-O—iso-propylidene-D-galactopyranose | 3'-1,2-propenyl | methyl | methyl |
| 6-O—1,2:3,4-di-O—iso-propylidene-D-galactopyranose | 2'-iso-propyl | " | " |
| 6-O—1,2:3,4-di-O—iso-propylidene-D-galactopyranose | sec-butyl | " | " |
| 6-O—1,2:3,4-di-O—iso-propylidene-D-galactopyranose | 3'-butyl | " | " |
| 6-O—1,2:3,4-di-O—iso-propylidene-D-galactopyranose | 2'-ethyl | H | H |
| 6-O—1,2:3,4-di-O—iso-propylidene-D-galactopyranose | methyl | H | H |

Still other compounds of the general formula M₂—O—Y wherein Y is a cyclic monovalent nitrogen-containing organic radical or residue, which may be used in the method of the invention are as follows:

| Monosaccharide Residue M₂ | Substitutent (Y) | |
|---|---|---|
| | Cyclic Radical | Substituent on the Cyclic Radical |
| 3-O—1,2-O—isopropylidene-D-glucofuranose | 4'-piperidyl | H |
| 3-O—1,2-O—isopropylidene-D-glucofuranose | 3'-piperidyl | methyl, H |
| 3-O—1,2-O—isopropylidene-D-glucofuranose | 2'-piperidyl | " |
| 3-O—1,2-O—isopropylidene-D-glucofuranose | 3'-pyrrolidyl | " |
| 3-O—1,2-O—isopropylidene-D-glucofuranose | 2'-pyrrolidyl | " |
| 6-O—1,2-O—isopropylidene-D-galactopyranose | 4'-piperidyl | H |
| 6-O—1,2-O—isopropylene-D-galactopyranose | 3'-piperidyl | methyl, H |
| 6-O—1,2-O—isopropylidene-D-galactopyranose | 2'-piperidyl | " |
| 6-O—1,2-O—isopropylidene-D-galactopyranose | 3'-pyrrolidyl | " |
| 6-O—1,2-O—isopropylidene-D-galactopyranose | 2'-pyrrolidyl | " |
| 3-O—1,2:3,6-di-O—iso-propylidene-D-glucofuranose | 4'-piperidyl | H |
| 3-O—1,2:3,6-di-O—iso-propylidene-D-glucofuranose | 3'-piperidyl | methyl, H |
| 3-O—1,2:3,6-di-O—iso-propylidene-D-glucofuranose | 2'-piperidyl | " |
| 3-O—1,2:3,6-di-O—iso-propylidene-D-glucofuranose | 3'-pyrrolidyl | " |
| 3-O—1,2:3,6-di-O—iso-propylidene-D-glucofuranose | 2'-pyrrolidyl | " |
| 6-O—1,2:1,4-di-O—iso-propylidene-D-galactopyranose | 4'-piperidyl | H |
| 6-O—1,2:1,4-di-O—iso-propylidene-D-galactopyranose | 3'-piperidyl | methyl, H |
| 6-O—1,2:1,4-di-O—iso-propylidene-D-galactopyranose | 2'-piperidyl | " |
| 6-O—1,2:1,4-di-O—iso-propylidene-D-galactopyranose | 3'-pyrrolidyl | " |
| 6-O—1,2:1,4-di-O—iso-propylidene-D-galactopyranose | 2'-pyrrolidyl | " |

In general, the preparation of compounds of the formula M₁—O—Y described herein involves the formation of cyclic organo amine ethers or alkyl amine ethers of substituted cyclic organo amine ethers or alkyl amine ethers at selected positions on the desired nonderivatized monosaccharide, such as at position 1-O- or 3-O- or D-glucose, position 6-O- of D-galactose, and position 3-O- of D-fructose. Similarly, the preparation of compounds of the formula M₂—O—Y described herein involves the formation of the aforementioned types of ethers at selected positions on the desired monosaccharide derivative, such as at position 3-O- or 1,2-O-isopropylidene-D-glucofuranose or 1,2:5,6-di-O-isopropylidene-D-glucofuranose, position 6-O- of 1,2-O-isopropylidene-D-galactopyranose or 1,2:3,4-di-O-isopropylidene-D-galactopyranose, and position 3-O- of 1,2-O-isopropylidene-D-fructopyranose or 1,2:5,6-di-O-isopropylidene-D-fructopyranose. The condensation of the substituent substrate with the desired nonderivatized monosaccharide or the monosaccharide derivative at the desired position may be achieved by various prior art techniques. One method is described in U.S. Pat. No. 2,715,121, issued Aug. 9, 1955, to Glen, et al, the disclosure of which is incorporated herein by reference. The method described in this patent requires extreme reaction conditions and often gives low yields. The product purity is also less than satisfactory.

The preferred method of preparation is described in my U.S. Pat. No. 4,056,322, the disclosure of which is incorporated herein by reference, and involves much milder reaction conditions than employed in U.S. Pat. No. 2,715,121. The side reactions are minimized, the purity of the final product is greatly improved and the method may be adapted to a series of solvents having varying properties such as dioxane, tetrahydrofuran and benzene. The improved method involves the reaction of a monosaccharide derivative which is blocked with one or more organo groups in the hydroxyl group positions adjacent the desired position to be substituted. The blocked monosaccharide is dissolved in one of the foregoing solvents and is reacted with a halogenated organo amino compound having the desired carbon chain length and configuration in the presence of a base such as sodium hydroxide. The resulting products are compounds of the formula $M_2$—O—Y, which are blocked derivatives of the compounds $M_1$—O—Y of the invention. Selective removal of one or more blocking groups may be accomplished by hydrolysis under specific conditions resulting in a new product which is to be considered a compound suitable for use in this invention. The reaction of either the blocked compound or the hydrolyzed compound with organic or inorganic acids to form a salt thereof also results in a compound suitable for use in this invention.

It is understood that simple derivatives of the compounds described herein may be used in practicing the invention. Such derivatives may be prepared by prior art techniques and procedures. For example, the free amine compounds are basic and form organic acid salts and inorganic acid salts, and the resulting salts are useful in the method of the invention. The salts may be prepared by the usual prior art techniques, such as by adding the free amine compound to water and then adding the desired organic acid or mineral acid thereto in an amount sufficient to neutralize the free amine. Examples of suitable acids include HCl, HBr, $H_2SO_4$, $HNO_3$, benzoic acid, p-aminobenzoic acid, p-acetamidobenzoic acid, p-hydroxybenzoic acid, alkane sulfonic acids, p-toluene sulfonic acid, acetic acid, alkylcarboxylic acids, oxalic acid, tartaric acid, lactic acid, pyruvic acid, malic acid, succinic acid, gluconic acid and glucuronic acid. The aqueous solution of the resulting salt is evaporated to the volume necessary to assure precipitation of the salt upon cooling. The precipitated salt is recovered by filtration washed and dried to obtain a final amine salt product. The amine salts are often preferred for use in formulating the therapeutic compositions of the invention as they are crystalline and relatively nonhygroscopic. The amine salts are also better adapted for intramuscular injection than are the free amines.

Prior art blocking or derivatizing techniques may be employed such as acetonization and acetylation. Suitable prior art blocking or derivatizing methods are described in the aforementioned U.S. Pat. Nos. 2,715,121 and 4,056,322. The alcohols used to produce an acetal group may contain 1-18 and preferably 1-4 carbon atoms. Specific examples include methyl, ethyl, propyl, isopropyl, butyl, isobutyl, amyl, and isoamyl alcohols. In instances where an aldehyde or ketone is reacted with hydroxyl groups on adjacent carbon atoms, the initial compound may be dissolved in the desired aldehyde or ketone under anhydrous conditions and a Lewis acid catalyst is added in a catalytic quantity, such as 1% zinc chloride or anhydrous phosphoric acid. Often acetone is the preferred blocking or derivatizing agent, but aldehydes or ketones of much higher molecular weight may be used when desired such as those containing up to 18 carbon atoms and preferably 1-8 or about 2-4 carbon atoms. Specific examples of additional ketones include methyl ethyl ketone, diethyl ketone, ethyl propyl ketone and dipropyl ketone. Specific examples of aldehydes include acetaldehyde, propionaldehyde, and butyraldehyde. The reaction mixture is agitated at room temperature for a prolonged reaction period, such as 24-48 hours. The compound may be blocked or derivatized in a plurality of positions, such as the 1,2- and 5,6-positions. It is usually preferred to block or derivatize positions such as the 1,2-positions as the resulting partially blocked or derivatized compound is much less toxic than compounds blocked or derivatized in all available hydroxyl groups.

It is also possible to block or derivatize one or more free hydroxyl positions of the compound with an ester group, wherein the carboylic acid residue contains 1-18 and preferably about 1-3 carbon atoms. Specific examples of organic acids include formic acid, acetic acid, propionic acid and butyric acid. The ester derivatives likewise may be prepared following prior art techniques such as by reacting a carboxylic acid anhydride with the compound following prior art practices. Additionally, the $\alpha$ or $\beta$ alkyl derivatives of nonderivatized monosaccharides or of monosaccharide derivatives such as 2,3:5,6-di-O-isopropylidene-D-glucofuranoside may be prepared following prior art techniques. In this latter instance, the compound is dissolved in a dry alcohol having the desired carbon chain length with the aforementioned residua and reacted with the compound in the presence of a catalyst such as the hydrogen chloride of Dowax 5- H+ resin. While the above discussed derivatives are presently preferred, it is understood that still other simple derivatives may be prepared following prior art techniques and then used in practicing the present invention.

The groups used in derivatizing $M_2$ of the formula $M_2$—O—Y are preferably labil organo groups, such as acetal or ketal groups, which are easily hydrolyzable or otherwise easily removed from the residue of the monosaccharide. For best results, the derivatizing groups should be easily removed in situ following administering the compound $M_2$—O—Y to a warm blooded animal to thereby produce the active compound $M_1$—O—Y.

The compounds used in the method of the present invention may be administered to human patients or lower warm blooded animals to be treated either orally or by parenteral administration, and either with or without a pharmaceutically acceptable carrier. When the compound is to be administered orally, it may be admixed with a prior art filler and/or binder such as starch and a disintegrator, and the admixture may be pressed into a tablet of a size convenient for oral administration. Capsules also may be filled with a composition containing the compound, with or without a filler, and administered orally. Alternatively, a water solution or suspension of the compound, or an admixture thereof with a flavored syrup such as cherry syrup, may be administered orally. When the compound is administered by intramuscular injection, it is usually dissolved in a physiological saline solution which contains sodium chloride in sufficient concentration to make the overall solution to be injected isotonic to body fluids. A salt of the free amine is usually preferred in instances where the compound is administered by intramuscular injection. In treating some patients or when convenient, the salt form of the compound is aqueous solution may also be administered by nasopharyngeal spray. Administration also may be by means of a suppository in patients unable to retain medication administered by mouth. Suitable pharmaceutically acceptable carriers and techniques in addition to those mentioned above may be used when desired.

The dosage may be varied over extremely wide limits, as the compounds are effective at low dosage levels and are nontoxic and free of adverse side effects. The compounds may be administered in the minimum quantity which is effective, and the dosage may be increased as desired up to the maximum effective dosage tolerated by the patient. Animal toxicity data indicate that the limiting nontoxic dosage may be 100-1000 or more times the minimum effective dosage. As a general rule, oral drug toxicity does not appear until the dosage exceeds 10 grams per kilogram of body weight per day and thus it is not necessary to carefully control the dosage for patients sensitive to the prior art drugs. The compound is usually administered in an amount of about 0.001-1000 milligrams, or for better results about 0.01-500 milligrams, per kilogram of body weight per day, and preferably in an amount of about 0.1-100 milligrams per kilogram of body weight per day, over the period required for treatment. In some instances better results are obtained at dosage levels of about 1-20 milligrams, and best results at about 10 milligrams, per kilogram of body weight per day.

In accordance with a further variant of the invention, a novel synergistic composition is provided for use in the method of the invention in treating autoimmune diseases in warm blooded animals which includes therapeutically active ingredients I and II. The ingredient I is a substance selected from the previously described group consisting of ethereally monosubstituted monosaccharides having the formula $M_1$—O—Y, and/or an ethereal monosubstitution of monosaccharide derivatives having the formula $M_2$—O—Y; and/or pharmaceutically acceptable organic acid and inorganic acid salts thereof. Thus, the ingredient I is a compound as previously discussed and reference therefor may be had to the foregoing discussion. The ingredient II is a prior art substance known to be therapeutically effective to treat autoimmune diseases when administered alone to the warm blooded animal, and which is therapeutically compatible with ingredient I and forms a synergistic composition therewith.

Examples of suitable prior art drugs which are therapeutically effective in the treatment of autoimmune diseases such as the specific diseases and drugs therefor previously discussed, are well known and there are a number of publications on the subject. Reference may be had, for example, to authoritative publications on this subject, such as the *Physicians Desk Reference*, 31st Edition, published by Medical Economics, Oradell, N.J. (1977); *The Merck Index*, 9th Edition, edited by M. Windholz, published by Merck and Company, Inc., Raleigh, N.J. (1976); and *Pharmacological Basis of Therapeutics*, edited by Louis S. Goodman, et al, 4th Edition, published by MacMillan and Co., New York, (1970), the disclosures of all of which are incorporated herein by reference. These authoritative publications give the prior art medications which are useful for autoimmune diseased, the quantity of medication to be given, and the method of administering the medication. Thus, a person skilled in this art may by reference thereto select a medication, amount of the medication, and method of administering the medication, and then combine these prior art teachings with the teachings of the present invention in arriving at a synergistic composition for use in the present invention.

As a general rule, the active ingredients of the synergistic composition may contain on a weight basis about 5-95%, and preferably about 25-75%, and usually for best results approximately 45-55% of ingredient I, and the remainder ingredient II. It is understood that pharmaceutically acceptable carriers, fillers, and the like may be present as was discussed previously when ingredient I is administered alone. Also, the composition may be administered in accordance with the same procedures as discussed previously for ingredient I when used alone. The method of administering the synergistic composition also may be in accordance with the above mentioned authoritative texts when using ingredient II alone. The dosage level when using the synergistic composition may be such as to provide the same amount of ingredient I as discussed hereinbefore when using ingredient I alone, and/or the same amount of ingredient II as discussed in the authoritative texts. The synergistic composition should be administered in an amount to provide a quantity of ingredient II not in excess of the weight thereof recommended in the authoritative texts, but smaller amounts are usually effective such as approximately 5-75% or 10-60%, and preferably about 25-50% by weight of the quantity previously recommended. Inasmuch as ingredient II is much more toxic than the compounds of ingredient I, it is possible to achive comparable or much better therapeutic results with the synergistic composition at the same or lower level of toxicity. Markedly better therapeutic results are achieved at substantially the same toxicity level when using the full recommended dose of the much more toxic ingredient II and the full recommended dose of the non-toxic ingredient I. However, lower amounts of each may be used with a corresponding drop in the toxicity level thereby allowing effective therapeutic treatment to be given to patients which are sensitive to the prior art medications.

In view of the foregoing, it is apparent that the synergistic compositions of the present invention, as well as the variant of the method of the invention which utilizes the synergistic composition, produce many unusual and unexpected beneficial results. The prior art medications may be used in smaller amounts to gain their benefits in instances where the patient is sensitive thereto, and yet still obtain the full benefits of the non-toxic compounds of ingredient I. Surprisingly, the compounds of ingredient I are not only non-toxic and free of side effects, but they are also compatible with the prior art drugs. Thus ingredient I may be administered in combination with ingredient II without noticeably increasing the overall toxicity level or otherwise adversely affecting the patient.

The aforementioned compounds of ingredient I alone or the overall synergistic composition may be administered either before, during or after appearance of the symptoms of the autoimmune disease. In some instances, it is preferred that the patient be treated either permanently or throughout the period of time necessary to prevent or suppress symptoms. This procedure is essentially effective in the treatment of rheumatoid arthritis, wherein it is often preferred that patients be placed on a chronic dose of medication throughout the winter or other seasons when the symptoms are aggravated. The method of the invention is also very effective in treating acute attacks of autoimmune diseases.

The method and composition of the invention are especially useful in treating human patients, but lower warm blooded animals and especially lower mammals also may be treated. For example, domestic animals and pets such as horses, bovines in general, sheep, goats, swine, cattle, poultry, birds and fowls in general, dogs, cats and the like may be treated in accordance with the invention. The foregoing are collectively referred to herein as being warm blooded animals.

The invention is further illustrated by the following hypothetical examples.

EXAMPLE I

It is known that female NZB/W mice develop an autoimmune disease characterized by immune complex glomerulonephritis, antibodies to DNA and RNA, lupus erythematosus (LE) cells, and shortened life expectancy. These findings are also seen in human systemic lupus erythrmatosus.

In this study, female NZB/W mice, age 20 weeks and already manifesting autoimmunity, are given SM-1211 or SM-1213 ad libitum in the drinking water at concentrations of either 0.1 or 0.01 mg/ml over ten weeks, and the frequency of proteinuria and antibodies to DNA are monitored by prior art techniques. The drugs should significantly reduce both symptoms of autoimmune disease, a finding which would be significant because of the relationship of this animal disease model to human autoimmune pathology.

EXAMPLE II

Twenty-four patients with classical or definite longstanding rheumatoid arthritis who respond poorly to the usual antiinflammatory and analgesic drugs are divided into a placebo group and two drug treatment groups, and are treated for six months. None of these patients have received corticosteroids, antimalarials, cytostatic agents or gold compounds for six months prior to the study, and are removed from antiinflammatory and analgesic drugs during the period of the study. SM-1211 and SM-1213 are administered as 20 mg/kg two times daily. The results of this study should show that drug treatment with SM-1211 and SM-1213 strikingly reduces the number of active joints and reduces the sedimentation rate in all cases.

EXAMPLE III

The procedure described in EXAMPLE II is carried out again, except that during the period of the study the antiinflammatory and analgesic therapies are continued unchanged. The results of this study should show that treatment with SM-1211 or SM-1213 in combination with antiinflammatory and analgesic therapies strikingly reduces the number of active joints and reduces the sedimentation rate.

I claim:

1. A method of therapeutically treating a warm blooded animal afflicted with an autoimmune disease selected from the group consisting of rheumatoid arthritis, rheumatic fever, eczema or lupus erythematosis which consists essentially of administering to said warm blooded animal an amount effective to therapeutically treat the rheumatoid arthritis, rheumatic fever, eczema or lupus erythematosis of a compound selected from the group consisting of
   I. ethereally monosubstituted monosaccharides having the formula $M_1$—O—Y and therapeutically effective and pharmaceutically acceptable organic acid and inorganic acid salts thereof, and
   II. etheral monosubstitutions of monosaccharide derivatives having the formula $M_2$—O—Y and therapeutically effective and pharmaceutically acceptable organic acid and inorganic acid salts thereof,
   wherein:
   (1) $M_1$ is the residue of a non-derivatized hexose,
   (2) $M_2$ is the residue of a hexose which has been derivatized with a substance selected from the group consisting of
      (a) an alcohol containing 1–18 carbon atoms to produce an ether group at the site of an available hydroxyl residue,
      (b) an aldehyde containing 1–18 carbon atoms to produce an acetal group at site of an available hydroxy residue,
      (c) a ketone containing 1–18 carbon atoms to produce a ketal group at the site of an available hydroxyl residue, and
      (d) an organic acid residue containing 1–18 carbon atoms to produce an ester group at the site of an available hydroxyl residue, and
   (3) Y in each instance is selected from the group consisting of (a) piperidyl and pyrrolidyl, and
      (b) monovalent organic radicals having the formula

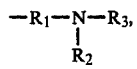

wherein $R_1$ is a divalent organic radical having a carbon chain length of 1–4 carbon atoms and $R_2$ and $R_3$ are selected from the group consisting of hydrogen and monovalent organic radicals having a carbon chain length of 1–4 carbon atoms.

2. The method of claim 1 wherein Y of said compound is

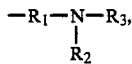

$R_1$ is a hydrocarbon having a carbon chain length of 1–3 carbon atoms, $R_2$ and $R_3$ are selected from the group consisting of hydrogen and hydrocarbons having a carbon chain length of 1–3 carbon atoms, and $M_1$ and $M_2$ are glucose or galactose.

3. The method of claim 1 wherein said compound is 3-O-3'-(N',N'-dimethylamino-n-propyl)-glucose or 3-O-3'-(N',N'-dimethylamino-n-propyl)-1,2-O-isopropylidene-glucose.

4. The method of claim 1 wherein said compound is 3-O-3'-(N',N'-dimethylamino-n-propyl)-D-glucose or 3-O-3'-(N',N'-dimethylamino-n-propyl)-D-1,2-O-isopropylidene glucofuranose.

5. The method of claim 2, wherein said compound is in the form of a salt of an acid selected from the group consisting of HCl, HBr, $H_2SO_4$, $HNO_3$, benzoic acid, p-aminobenzoic acid, p-acetamidobenzoic acid, p-hydroxybenzoic acid, alkane sulfonic acid, p-toluene sulfonic acid, lower alkyl monocarboxylic acids, oxalic acid, tartaric acid, lactic acid, pyruvic acid, malic acid, succinic acid, gluconic acid and glucuronic acid.

6. The method of claim 1, wherein said compound is in the form of a salt of an acid selected from the group consisting of HCl, HBr, $H_2SO_4$, $HNO_3$, benzoic acid, p-aminobenzoic acid, p-acetamidobenzoic acid, p-hydroxybenzoic acid, alkane sulfonic acid, p-toluene sulfonic acid, lower alkyl monocarboxylic acids, oxalic acid, tartaric acid, lactic acid, pyruvic acid, malic acid, succinic acid, gluconic acid and glucuronic acid.

7. The method of claim 4, wherein said compound is in the form of a salt of an acid selected from the group consisting of HCl, HBr, $H_2SO_4$, $HNO_3$, benzoic acid, p-aminobenzoic acid, p-acetamidobenzoic acid, p-hydroxybenzoic acid, alkane sulfonic acid, p-toluene sulfonic acid, lower alkyl monocarboxylic acids, oxalic acid, tartaric acid, lactic acid, pyruvic acid, malic acid, succinic acid, gluconic acid and glucuronic acid.

8. The method of claim 7 wherein said autoimmune disease is rheumatoid arthritis.

9. The method of claim 2 wherein said autoimmune disease is rheumatoid arthritis.

10. The method of claim 4 wherein said autoimmune disease is rheumatoid arthritis.

11. The method of claim 2 wherein said autoimmune disease is rheumatic fever.

12. The method of claim 3 wherein said autoimmune disease is rheumatic fever.

13. The method of claim 4 wherein said autoimmune disease is rheumatic fever.

14. The method of claim 2 wherein said autoimmune disease is eczema.

15. The method of claim 3 wherein said autoimmune disease is eczema.

16. The method of claim 4 wherein said autoimmune disease is eczema.

17. The method of claim 2 wherein said autoimmune disease is lupus erythematosis.

18. The method of claim 3 wherein said autoimmune disease is lupus erythematosis.

19. The method of claim 4 wherein said autoimmune disease is lupus erythematosis.

* * * * *